United States Patent [19]

Walsh et al.

[11] 4,231,661
[45] Nov. 4, 1980

[54] RADIAL SCANNER

[75] Inventors: J. William Walsh, Baltimore, Md.; Raymond E. Bietry, Jr., Lake Shawnee, N.J.

[73] Assignee: Becton, Dickinson & Company, East Rutherford, N.J.

[21] Appl. No.: 944,179

[22] Filed: Sep. 20, 1978

[51] Int. Cl.³ ............................................ G01N 21/01
[52] U.S. Cl. ..................................... 356/340; 250/574
[58] Field of Search ....................... 356/335, 336, 340; 250/574

[56] References Cited
U.S. PATENT DOCUMENTS
3,520,586  7/1970  Bousky .................................. 350/6.7

FOREIGN PATENT DOCUMENTS
1457743  12/1976  United Kingdom ..................... 356/336

Primary Examiner—John K. Corbin
Assistant Examiner—Bruce Y. Arnold
Attorney, Agent, or Firm—Burns, Doane, Swecker & Mathis

[57] ABSTRACT

The disclosure relates to a radial scanner usable for scanning a small volume of a test sample in a differential light scattering analyzer. In the scanner a beam of collimated light impinges on a rotating planar mirror located above or below the test sample on an axis passing through the small volume. A beam of light reflected from the mirror sweeps a conical mirror, having its reflecting surface curved about a reference axis passing through the small volume. The small volume is scanned by a beam of light reflected from the conical mirror at different radial angles as the planar mirror is rotated.

12 Claims, 8 Drawing Figures

RADIAL SCANNER

BACKGROUND OF THE INVENTION

The present disclosure is directed to an optical scanner for a differential light scattering analyzer for microparticles, and is particularly useful in the automated testing of the response of bacteria to therapeutic agents, such as antibiotics.

The principles of operation of a differential light scattering analyzer for microparticles are discussed in detail in U.S. Pat. No. 3,770,351 to Wyatt, issued Nov. 6, 1973 and U.S. Pat. No. 3,928,140 to Wyatt et al, issued Dec. 23, 1975, which patents are hereby incorporated by reference.

Briefly, a differential light scattering analyzer may be employed to rapidly analyze microparticles by measuring the light scattering properties of the particles. In the analyzer a collimated beam of electromagnetic radiation, such as from a laser, is directed at a test sample containing the particles. One or more detectors are employed to produce signals representing the scattered light intensity from the microparticles at different angles relative to the incident laser beam. Where the microparticles are bacteria, it has been observed that the differential light scattering properties provide indicia of the growth of the bacteria and/or its morphology.

The present invention relates to a scanner for scanning a small volume of microparticles at different radial angles. The disclosed scanner is well adapted for use in an automated differential light scattering analyzer, capable of quickly and accurately making differential light scattering measurements for a large number of test samples.

A differential light scattering analyzer, known in the prior art, is illustrated in the above-referenced U.S. Pat. No. 3,770,351 to Wyatt. Wyatt discloses directing a highly collimated incident beam of light at a test sample located at the center of a test chamber. A plurality of detectors are mounted about the test chamber at equal radial distances from the test sample. Scattered radiation is sensed by each of these light detectors, each detector sensing the light intensity at a different, fixed, observation angle with respect to the incident beam.

The system disclosed by Wyatt has the disadvantage in that it requires a detector to be located at each angular location about the test sample at which a scattering intensity measurement is to be made. Since the effectiveness of the analyzer is increased by making highly accurate intensity measurements at a large number of different radial angles (e.g. 100 different angles), to achieve this accuracy, the Wyatt system would require the use of a large number of detectors, calibrated with respect to one another.

Accordingly, it is an object of the present invention to provide a simply and inexpensively fabricated scanner for producing an accurate measurement of the intensity of scattered radiation from a microparticle test sample at a number of different scattering angles.

It is another object of the present invention to provide a simply and inexpensively fabricated radial scanner which employs a single photodetector.

Another differential light scattering analyzer known in the prior art is illustrated in the above-referenced U.S. Pat. No. 3,928,140 to Wyatt et al. In the Wyatt et al patent, an incident, collimated beam of light from a laser is directed at a stationary test sample containing microparticles. A detector periscope, comprising a number of optical elements, directs scattered light to a photomultiplier tube. The periscope is rotated through an arc about the test sample to produce signals at the photomultiplier representing the scattered light intensity as a function of the angle of scattering relative to the incident laser beam. The periscope is driven back and forth in an arc around the test sample through an angular range of from 30° to 130° with respect to the direction of the incident laser beam.

This Wyatt el al system has the disadvantage in that the sensitive periscope optics must be driven through the 100° arc, then abruptly reversed in direction and driven backwards through the 100° arc to perform a scan of the test sample. In order to provide rapid measurement in an automated high volume analyzer, the periscope would have to be driven at a high speed, thereby increasing the potential for misaligning of the optics. The drive mechanism for rotating the periscope must be manufactured to very high tolerances to prevent objectionable eccentricity in the arc through which the periscope moves and to prevent misalignment of the periscope with respect to the test sample during a portion of the arc. Moreover, the control system for the motor driving the periscope through the arc must be coordinated with the analyzer circuits so that the test is properly sequenced and so that intensity measurements are properly identified with the particular angular positions at which they are made.

Accordingly, it is an object of the present invention to provide an optical scanner for a differential scattering analyzer which is capable of accurately scanning a test sample from different radial angles at a high rate of speed.

It is another object of the present invention to provide a radial scanner for a differential light analyzer which employs a small number of moving optical elements.

It is another object of the present invention to provide a radial scanner for a differential light analyzer which minimizes the acceleration and deceleration of optical elements used therein.

It is yet another object of the present invention to provide a radial scanner for a differential light scattering analyzer which minimizes the distance of travel of the moving optical elements.

A number of scanners are known in the prior art which employ rotating planar mirrors to reflect light on a curved stationary mirror. Such scanners are shown for example in U.S. Pat. No. 3,469,030 to Priebe, U.S. Pat. No. 3,520,586 to Bousky and U.S. Pat. No. 4,029,389 to Runciman. However, such scanners are concerned with scanning a line or scanning a generally planar surface with a focused beam of light. Such systems are not adapted to scan a small volume or point from different radial angles and are not adapted for use in a detector of scattered light from a scanned volume. Since these systems cannot perform radial scanning, they cannot, of course, function to perform the radial scanning required for differential scattering analysis.

Accordingly, it is the object of the present invention to provide a radial scanner employing a single rotating mirror.

These and other objects and features of the invention will become apparent from the claims and from the following description when read in conjunction with the accompanying drawings.

THE FIGURES

DETAILED DESCRIPTION

Figure 4:
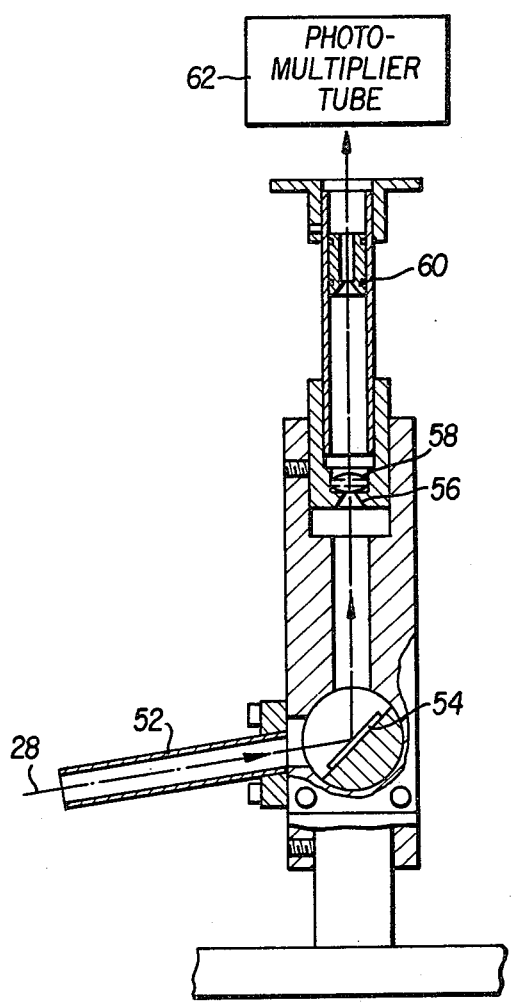
FIG. 4 is a side elevational view of a scattered light detector.

A preferred embodiment of the radial scanner of the present invention and portions thereof are shown in FIGS. 1, 2, 3, and 3a wherein like structures and features are identified with like numerals. The radial scanner may be employed as a part of a differential light scattering analyzer. Such a differential light scattering analyzer may include a source of a collimated beam of radiant energy. Advantageously, such a source beam may be a coherent, monochromatic beam provided by a laser. The source beam is directed at a generally planar mirror which is rotated to sweep a reflected beam along a scanning line. A conically curved mirror is located along at least a portion of the scanning line described by the beam reflected from the rotating planar mirror. The conically curved mirror reflects the swept beam generally radially inwardly through a range of scanning angles toward a scattering test sample which is located approximately on the cone axis of the conically curved mirror. A detector is employed for detecting the intensity of radiant energy scattered by the test sample through the field of vision of the detector, defined by an optical window of the detector. The detector is stationary in the frame of reference of the conically curved mirror and test sample. A detector suitable for use in the differential light scattering analyzer described herein, is shown in FIG. 4 and described below.

Figure 5:
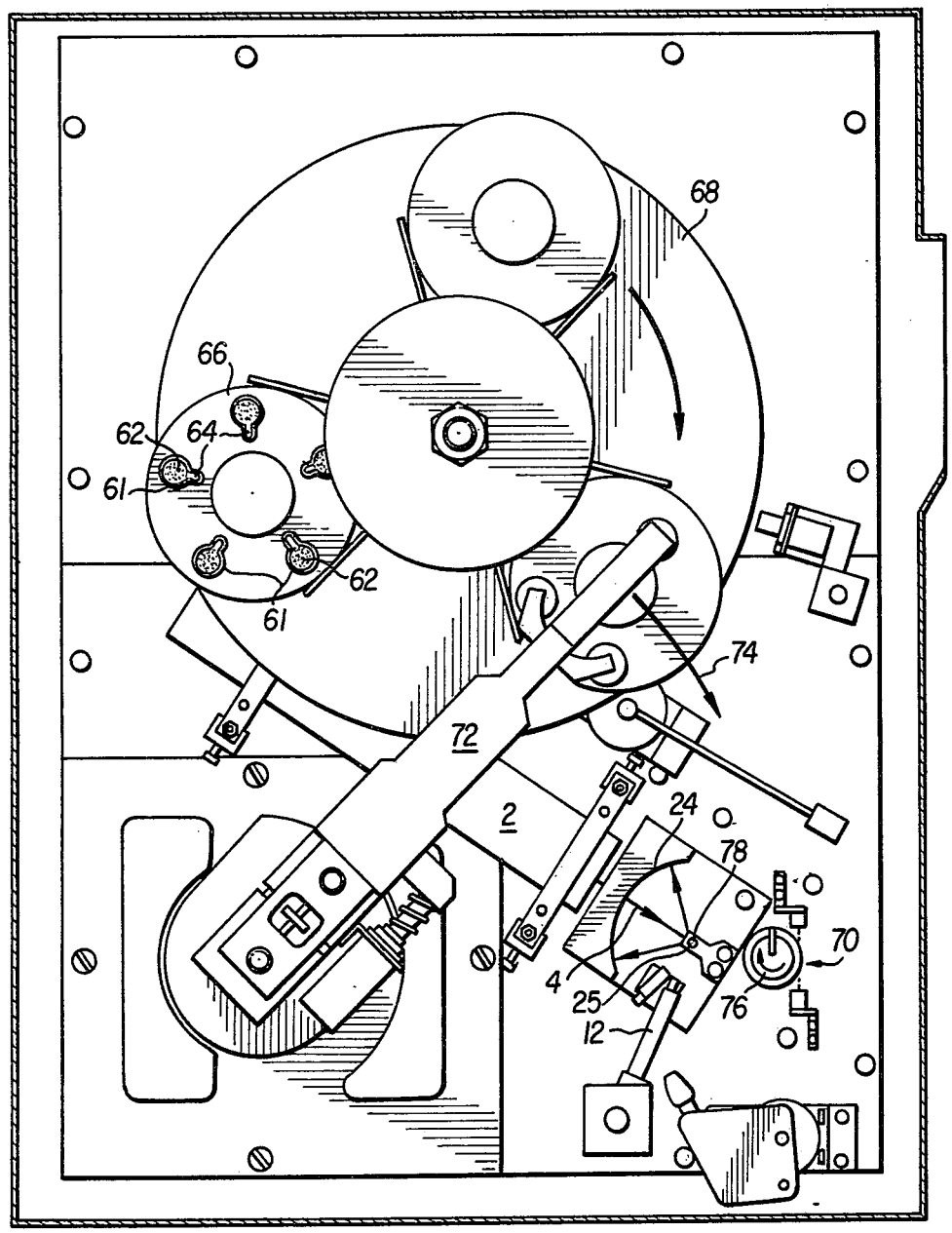
FIG. 5 is a plan view of an antibiotic susceptibility tester employing a differential light scattering analyzer with a radial scanner.

The differential light scattering analyzer and radial scanner discussed in connection with FIGS. 1 through 3 may, advantageously, be employed in an automated antibiotic susceptibility tester. Such a tester is illustrated in FIG. 5. The automated antibiotic susceptibility tester is adapted for quickly and accurately analyzing the light scattering properties of bacterial samples contained in a large number of sample holders or cuvettes, such as the cuvette shown in FIG. 6. The samples are exposed to various antibiotics. The automated tester sequentially loads cassettes of the cuvettes into a test station where the cuvettes are sequentially positioned at the scanning center of the radial scanner, at which time differential light scattering measurements are made for the individual cuvette to determine bacterial response to the antibiotics.

Figures 1, 1A:
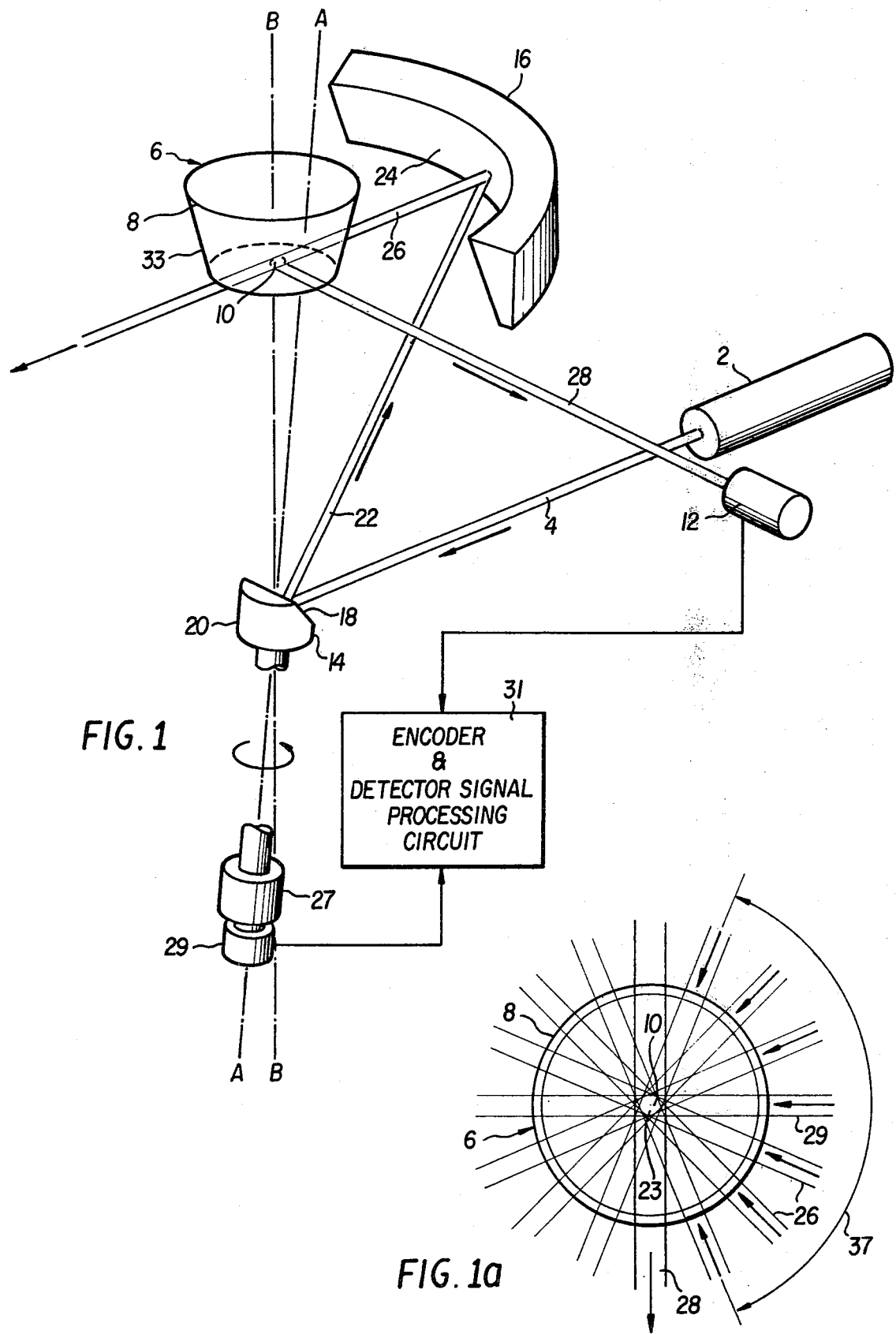
FIG. 1 is a schematic perspective view of a differential scattering analyzer employing a radial scanner of a preferred embodiment of the present invention.
FIG. 1a is a schematic plan view of a detail of FIG. 1.

FIG. 1 is a perspective view of a radial scanner in a differential scattering analyzer apparatus. The apparatus includes a source 2 of a beam 4 of collimated radiant energy. In a preferred embodiment the source 2 may be an optical laser. Radiant energy from the source 2 is directed toward a test sample 6 of microparticles, located within a transparent container 8. Radiant energy scattered by microparticles in the test sample is detected by photodetector 12.

In a preferred embodiment of the present invention an incident beam of radiant energy from the source 2 scans the test sample 6 at different radial angles. The scanning is facilitated by a light deflecting element 14 which sweeps the optical surface of a curved reflecting element 16 as the deflecting element and reflecting element are rotated with respect to one another.

In the embodiment shown in FIG. 1, the deflecting element 14 comprises a planar mirror 18 mounted on a rotor 20. The rotor 20 may be rotated about an axis A—A so that a beam 22 of radiant energy reflected by the planar mirror 18 sweeps the surface of the curved reflecting element 16.

The light reflecting element 16 may be formed with a reflecting surface 24 which is curved about a reference axis B—B, passing through the test sample. As shown in FIG. 1 the reflective surface 24 of the reflective element 16 may be the interior surface of a conical segment, the axis of the cone being the reference axis B—B.

In the embodiment shown in FIG. 1, the rotating deflecting means 14 is located at the intersection of axes A—A and B—B at a location displaced from the test sample container 8. The test sample container 8 may be located in the same place as the curved reflecting element 16 and the photodetector 12. The deflecting element 14 and the radiant energy source may be located in a plane parallel to and displaced from the plane of the container, reflecting element, and detector.

It will be apparent from FIG. 1 that an incident, radially scanning beam 26 of radiant energy reflected by the reflecting element 16 will, illuminate a generally cylindrical portion of the microparticles located in the sample container 8. Advantageously, the incident beam 26 may be scanned through a predetermined angular range, typically a 100° arc, which may correspond to the arc subtended by the interior conical surface segment of the reflecting surface 24. It will be readily understood that the incident beam 26 will illuminate a small, approximately spherical volume 10 of the test sample throughout the scanning arc, but, assuming that multiple scattering does not occur, will illuminate other portions of the test sample only during a portion of the scanning arc. The continuously illuminated volume 10 is located on the cone axis B—B at the scanning center of the apparatus with respect to which the incident beam 26 is radial throughout the scanning arc.

The photodetector 12 may employ a suitable aperture and lens system to define a small optical window to facilitate detection of scattered light received along a generally cylindrical beam 28. It should be understood that light is scattered in virtually every direction from the test sample. For convenience the light scattered to the detector is referred to as the "scattered beam". The scattered beam 28 originates at the illuminated volume 10 of the test sample 6. A photodetector suitable for use with the embodiment of FIG. 1 is described in greater detail in connection with FIG. 4.

The scanning of the small volume 10 of the test sample is described in greater detail with reference to FIG. 1a. The volume scanned at any one scanning angle, for example, the scanning angle of beam 29, will be the volume defined by the intersection of the beam 29 and the scattered beam 28. It will be readily understood that the approximately spherical volume 10, will be illuminated at all the scanning angles through the angular range indicated by the double-headed arrow 31, though additional volumes in the test sample may be illuminated at any one particular scanning angle.

The container 8 of FIGS. 1 and 1a has a circular cross section centered on the cone axis B—B and is frustoconical in shape. In order to center the container in the scanner, each container may be provided with a conical indentation 23 (FIG. 1a) for mating with a fixed, conical stylus. Significant advantages are obtained by employing such an arrangement and by accurately, radially scanning the test sample through a range of angles in substantially the same plane. First, to the extent that optical surfaces of the sloping side walls 33 reflect the incident scanning beam 26, such reflection is out of the plane of the detector. Second, nearly the same volume of the test sample is scanned at all scanning angles, which means that the detected scattering is caused by nearly the same population of microparticles at each scanning angle. Third, by scanning a volume which is small with respect to the total volume of the test sample and located at the center of the sample and container, distorting refraction effects on the incident and scattered beams are minimized, provided the incident scanning beam is at all times radial to the container. When these conditions are met the incident beam and scattered beam are nearly perpendicular to a tangent to the circular cross section of the container. Any reflected or refracted component of the incident beam will be radial and will not therefore propagate to the detector.

In operation, microparticles to be analyzed are placed within the container 8, and the container 8 is then inserted in the differential light scattering analyzer as shown in FIG. 1 so that the scanning center lies within the test sample 6. The rotor 20 is continuously rotated at a rapid rate, typically five times per second, so that the incident scanning beam 26 repeatedly and rapidly scans the test sample 6 through a predetermined angular range, typically a 100° range. Light is scattered to the detector 12 as the incident beam scans through the angular range. It will be readily apparent that through the remaining 260° of rotation of the rotor 20, no incident beam will fall on the test sample and, therefore, no scattered light should be detected by the photodetector 12.

A motor 27 may be employed to rotate the rotor 20, and an encoder 29 may be coupled to the rotor 20 for producing a signal related in value to the angle between the incident beam 26 and the scattering beam 28. The encoder may be a suitable conventional angular optical encoder. An output signal from the photodetector 12 and the output signal from the encoder 29 may be applied to a circuit 31 for measuring and recording the intensity of the light detected by the photodetector for a plurality of scattering angles. This signal may be used to analyze properties of the microparticles contained in the test sample 6.

Figure 2:
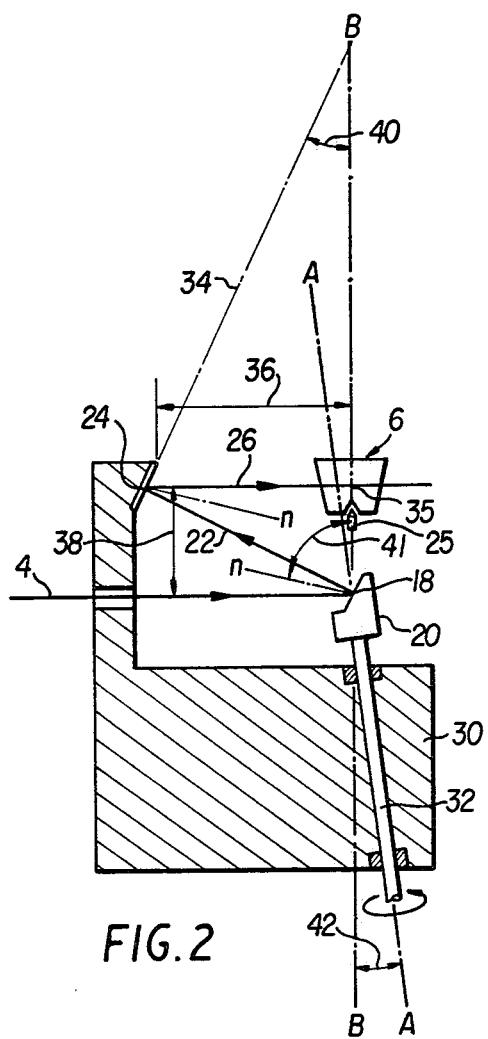
FIG. 2 is a cross-sectional elevation of a portion of the radial scanner of FIG. 1.

FIG. 2 is a cross-sectional elevation of a portion of the radial scanner depicted schematically in FIG. 1, showing the geometry of the arrangement of the mirrors. As shown in the Figure the curved reflecting surface 24 may be formed in a base member 30 which also supports a shaft 32 on which the rotor 20 is rotated. This arrangement facilitates accurate alignment of the various optical elements in the scanner so that the incident beam 26 scans at a substantially constant height measured along the axis B—B, and at a generally uniform angular velocity throughout the scan.

The reflecting surface 24 may be formed by depositing reflective material onto the base member 30. As shown in FIG. 2, the reflective surface 24 is an interior surface of a conical segment, with a cone axis B—B passing through the test sample 6. A projection of the surface of the cone is indicated by the dashed line 34.

The dimensions and orientations of the elements of the scanner may be selected to minimize deviation of the incident beam 26 from a target point 35 in the test sample 6 on the axis B—B. For example, the radius of the conical mirror in the plane of the incident beam 26 may be selected to be 1.875 inches. This dimension is indicated by the double headed arrow 36. The elevation of the incident beam 26 above the source beam 4, indicated by double headed arrow 38, may be 0.485 inches. The angle between the axis B—B and the slant height 34 of the cone (and the conical mirror) may be 15°. This angle is indicated by the double headed arrow 40. Finally, an angle 41 between the axis B—B and an axis n, normal to the mirror 19, may be 75° when the mirror 18 is located at the midpoint in the scanning range. Given these parameters, calculations indicate that the optimum angle of inclination of the axis of rotation A—A from the axis B—B is 8.415°. This angle is indicated by the double head arrow 42. This angle 42 is selected to minimize the error in height of the incident beam 26, measured along the axis B—B. When the axis A—A and B—B are inclined at that angle, the error in height is suitably small and does not induce substantial inaccuracy in the scattering measurements.

In order to center the container 8 in the scanner, a conical stylus 25, fixed in the scanner along the axis B—B of the conical mirror, may be provided for mating with the conical indentation 23 in the container 8. Thus, if the container is moved downwardly into the scanner, (i.e. generally along the axis B—B), the container will center itself on the stylus.

It will be readily apparent from FIG. 1 that the positions of the radiant energy source 2 and the detector 12 may be interchanged so that the beam from the source impinges on the test sample from a fixed direction and so that the scattered light is scanned through a range of angles.

Figure 3:
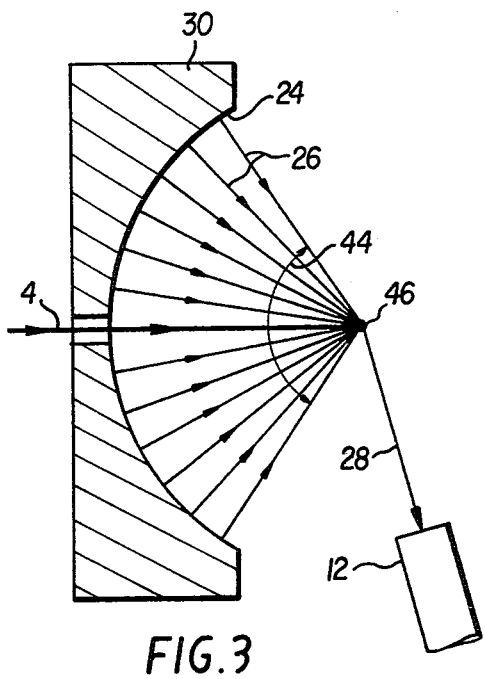
FIG. 3 is a plan view of a portion of the radial scanner shown in FIG. 2.

FIG. 3 is a plan view of a portion of the radial scanner shown in FIG. 2. FIG. 3 illustrates the range of scanning angles (indicated by double headed arrow 44) through which the incident beam 26 is scanned radially with respect to a scanning center 46 in the test sample. In a preferred embodiment of the present invention, intensity of the scattered beam 28 may be detected by the photodetector 12 for 100 discrete scanning angles corresponding to 1° increments in the scan of the incident beam 26 with respect to the scattered beam 28.

Figure 3A:
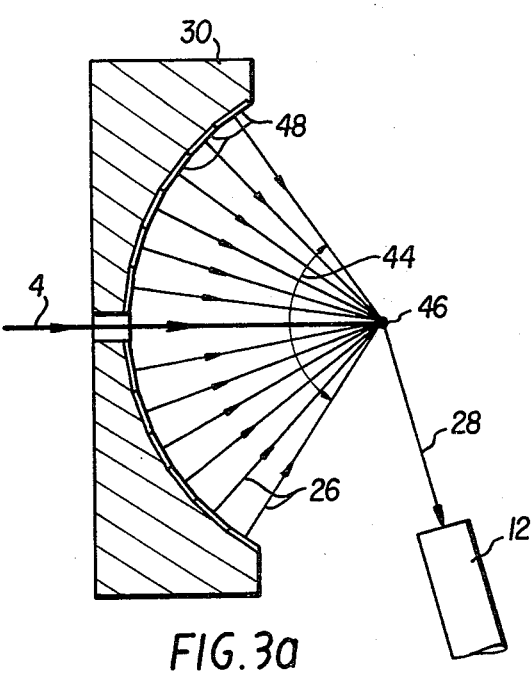
FIG. 3a is a plan view of an alternate embodiment of the portion of the radial scanner shown in FIG. 3.

In an alternate embodiment, shown in FIG. 3a, the reflective surface may be formed by placing a plurality of small planar mirrors 48 on the curved surface of the base member 30 thereby forming a faceted mirror. The use of a faceted mirror eliminates the slight focusing of the incident beam caused by a mirror with a smooth curvature. In the case that a faceted reflecting element is used to provide measurements at 100 scanning angles, the reflective surface 24 would comprise 100 planar mirrors placed adjacent one another corresponding to the 1° angular increments through the 100° arc.

In connection with FIGS. 1 and 2, an embodiment of the present invention has been described as having a rotating mirror 18 which rotates on an axis A—A, inclined with respect to the scanner reference axis B—B. However, a scanner may be constructed in accordance with the teachings of the present invention with rotating mirror 18 having an axis of rotation lying on the reference axis B—B.

In such a case, the reflecting surface 24 may be modified to insure that the volume of the test sample is scanned throughout the range of scanning angles by beams 26, all lying in the scanning plane (i.e. a plane perpendicular to the reference axis B—B), while such a reflecting surface would still be curved about the reference axis B—B; advantageously, the reflecting surface would not be a conical surface segment having a cone axis B—B as shown in FIGS. 1 and 2. Instead, for example, the reflecting surface could be a multifaceted mirror similar to that shown in FIG. 3A, except that adjacent facets would have slightly different inclinations with respect to the axis B—B and slightly different distances from the scanning center, selected so that the beams 26 reflected by each facet would all be reflected toward the scanning center 46 and in the plane of scanning.

In FIG. 4 a stationary photodetector 12 is depicted which may be advantageously used in the radial scanner described in connection with FIGS. 1 through 3. As shown in the Figure, the scattered beam 28 from the test sample enters the detector 12 through an input tube 52. The beam is reflected by a mirror 54 and subsequently passes through an input aperture 56. A convex lens 58 focuses the beam and the beam passes through a second aperture 60. This beam impinges on a radiant energy detector, which is preferably a photomultiplier tube 62. However, other types of radiation detectors such as photoactive semiconductors may be employed in place of the photomultiplier tube.

FIG. 5 is a plan view of an automated antibiotic susceptibility tester employing the radial scanner discussed in connection with FIGS. 1 through 3 and employing the detector 12 discussed in connection with FIG. 4.

Figure 6:
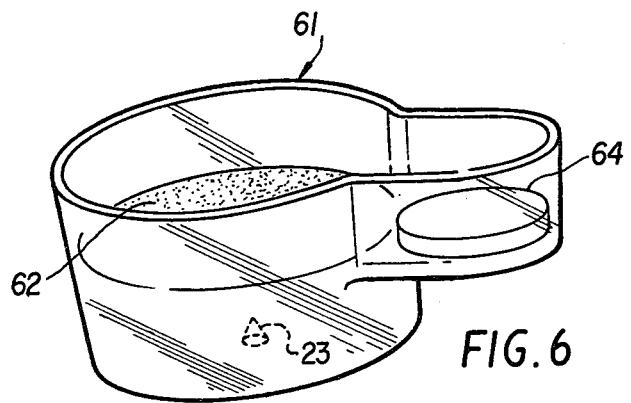
FIG. 6 is a perspective view of a cuvette which may be employed in the antibiotic susceptibility tester of FIG. 5.

In the apparatus shown in FIG. 5, bacterial samples are placed in a plurality of cuvettes 61. FIG. 6 is an enlarged perspective view of a single cuvette such as may be employed in the apparatus of FIG. 5. The cuvettes may contain a growth medium 62 for supporting the growth of bacteria. The effect of antibiotics on the growth of the bacteria may be tested by exposing the bacteria to antibiotic treated pads 64. As shown most clearly in FIG. 6, the pads 64 are placed in communication with the growth medium 62 in a space adjacent to the growth medium. Control samples are left unexposed to the antibiotics. The small volume 10 of the cuvette is scanned in the analyzer.

With continued reference to FIG. 5, a plurality of the cuvettes 62 are shown loaded in a cassette 66. In turn, a number of these cassettes are loaded on a carrousel 68 contained within the automated antibiotic susceptibility tester.

After a monitored period of incubation, a cassette may be automatically unloaded from the carrousel 68 and positioned at the test station 70 by means of an unloading arm 72 which moves in the direction indicated by the arrow 74. The center of the cassette, when positioned at the loading station, is located at the center of a cassette turntable 76, which may be rotated in the direction indicated by the arrow to sequentially place the cuvettes 61 in a test position 78 so that the scanning center of the radial scanner lies at the axial center of the cuvette.

The radial scanner employed in the automated antibiotic susceptibility tester is similar to that shown in FIGS. 1-3 and like numerals have been employed to identify like structures and features.

Once a cuvette is located in the test position, the rotating mirror (not shown) scans the curved reflecting surface 24 (FIG. 1), with a beam 4 of collimated light from the laser 2. The reflecting surface reflects the beam radially inwardly toward the test sample contained by the cuvette. The test sample is scanned through the range of scanning angles and light scattered by the test sample in the cuvette is detected by the detector 12, described in detail in connection with FIG. 4. Subsequent cuvettes may be analyzed by rotating the turntable 70 to place an adjacent cuvette at the test position 78 and repeating the scanning operation. In this way, a large number of cuvettes may be rapidly and accurately scanned to obtain differential light scattering data for the test samples therein.

The principles, preferred embodiments and modes of operation of the present invention have been described in the foregoing specification. The invention which is intended to be protected is not, however, to be construed as limited to the particular forms disclosed, since these are to be regarded as illustrative rather than restrictive. Variations and changes may be made by those skilled in the art without departing from the spirit and scope of the present invention.

What is claimed is:
1. A radial scanner comprising:
   a source of a beam of radiant energy;
   a means for deflecting the beam of radiant energy, said deflecting means being located on a reference axis;
   means for rotating the deflecting means to thereby sweep the deflected beam; and
   means, having a planar surface curved about the reference axis for reflecting the swept, deflected beam; whereby a beam reflected by the reflecting means radially scans a test sample container located on the reference axis and displaced from said deflecting means, said scanning being affected through a range of angles lying in substantially the same plane.

2. A scanner for a differential light scattering analyzer comprising:
   a source of a collimated beam of radiant energy;
   a generally planar reflecting means for reflecting the beam of radiant energy from the source;
   means for rotating the planar reflecting means, to thereby sweep the reflected beam;
   a conically curved reflecting means for reflecting the swept beam generally radially inwardly through a range of scanning angles toward a scattering test sample disposed approximately on the cone axis of the conically curved reflecting means; and
   detecting means for detecting radiant energy scattered by the test sample from the beam reflected from the conically curved reflecting means, the detecting means having an optical window which detects the scattered radiant energy from a volume within the test sample on which the beam reflected from the conically curved reflecting means impinges through the range of scanning angles, wherein the axis of rotation of the rotated reflecting means is disposed at an acute angle with respect to said cone axis, said acute angle being selected to minimize deviation of the radially inwardly reflected scanning beam from a plane throughout the range of scanning angles.

3. The analyzer of claim 2 wherein the optical window of the detecting means and the test sample lie generally in the plane of the radially inwardly reflected scanning beam.

4. The analyzer of claim 2 wherein said rotating means continuously rotates the planar reflecting means through 360°.

5. The analyzer of claim 2 wherein the beam from the source and a normal to the plane of the planar reflecting means lie in the same plane at a point in the rotation of the planar reflecting means corresponding to the midpoint in the range of scanning angles.

6. The analyzer of claim 2 wherein the source of radiant energy is a laser.

7. A scanner for a differential light scattering analyzer comprising:
   a source of a collimated beam of radiant energy;
   a generally planar reflecting means for reflecting the beam of radiant energy from the source;
   means for rotating the planar reflecting means, to thereby sweep the reflected beam;
   a conically curved reflecting means for reflecting the swept beam generally radially inwardly through a range of scanning angles toward a scattering test sample disposed approximately on the cone axis of the conically curved reflecting means; and detecting means for detecting radiant energy scattered by the test sample from the beam reflected from the conically curved reflecting means, the detecting means having an optical window which detects the scattered radiant energy from a volume within the test sample on which the beam reflected from the conically curved reflecting means impinges through the range of scanning angles, wherein the deflecting means and the test sample are located on the cone axis of the conically curved reflecting means and wherein the axis of rotation of the planar reflecting means intersects the cone axis at at least one point displaced from the test sample.

8. The analyzer of claim 2 wherein the conically curved reflecting means comprises a plurality of planar mirror elements located adjacent one another and lying generally on the interior of a conical surface segment.

9. In an apparatus for detecting the intensity of light scattered by microparticles in a test sample container at a plurality of angles between a beam incident on the test sample from a source of collimated light and a beam of light scattered from the test sample and detected by a photo detector, the improvement comprising:
   means for reflecting either the incident beam or the scattered beam, having a conical reflecting surface curved at a constant radius about a point on a reference axis passing through the test sample container;
   light deflecting means for scanning the light reflecting means; and
   means for rotating the deflecting means relative to the curved reflecting means whereby the angle between the incident beam and the scattered beam is varied.

10. A scanner for a differential scattering analyzer comprising:
    a source of an incident beam of collimated radiant energy;
    a photodetector for detecting a beam scattered by microparticles in a test sample illuminated by the incident beam;
    means for reflecting one of the incident beam and the scattered beam, having a planar surface curved about a reference axis passing through a small volume of microparticles in a test sample of microparticles;
    light deflecting means for scanning the light reflecting means; and
    means for rotating the deflecting means relative to the reflecting means so that the angle between the incident beam and the scattered beam is varied through a range of angles lying in substantially the same plane, wherein the test sample of microparticles is contained in a container having a circular cross section in the plane of the scanning angles and centered on the reference axis.

11. The scanner of claim 10 further comprising a conical stylus adapted to mate with a conical indentation in the container to center the container on the reference axis.

12. The scanner of claim 10 further comprising:
    means, coupled to said rotating means, for detecting the angle between the incident beam and the scattered beam; and
    means responsive to the angle detecting means and the photodetector for recording the intensity of the light scattered to the optical window of the photodetector as a function of the angle detected by the angle detecting means.

* * * * *